United States Patent
Koria et al.

(10) Patent No.: US 8,940,868 B2
(45) Date of Patent: Jan. 27, 2015

(54) ELASTIN BASED GROWTH FACTOR DELIVERY PLATFORM FOR WOUND HEALING AND REGENERATION

(75) Inventors: Piyush Koria, Tampa, FL (US); Martin L. Yarmush, Newton, MA (US); Yaakov Nahmias, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 777 days.

(21) Appl. No.: 12/899,141

(22) Filed: Oct. 6, 2010

(65) Prior Publication Data

US 2011/0092422 A1    Apr. 21, 2011

Related U.S. Application Data

(60) Provisional application No. 61/249,682, filed on Oct. 8, 2009.

(51) Int. Cl.
| | | |
|---|---|---|
| C07K 19/00 | (2006.01) | |
| A61K 38/16 | (2006.01) | |
| C07K 14/475 | (2006.01) | |
| C07K 14/78 | (2006.01) | |
| A61K 38/00 | (2006.01) | |

(52) U.S. Cl.
CPC ............... *C07K 14/475* (2013.01); *C07K 14/78* (2013.01); *A61K 38/00* (2013.01); *C07K 2319/70* (2013.01)
USPC ........................................................ 530/350

(58) Field of Classification Search
None
See application file for complete search history.

(56) References Cited

U.S. PATENT DOCUMENTS 4,885,163 A * 12/1989 Shaar et al. .................... 514/8.5
2007/0265197 A1   11/2007 Furgeson et al.

FOREIGN PATENT DOCUMENTS

WO    WO 2008/030968 A2 *  3/2008  ............. A61K 38/17

OTHER PUBLICATIONS

PubMed KGF sequence, from http://www.ncbi.nlm.nih.gov/protein/P21781.1, pp. 1-3, accessed Aug. 1, 2013.*
Megeed et al, Self-Assembling Multifunctional Nanoparticles from Elastin-Like Polypeptides, PMSE Preprints, 2007, 96, pp. 1-2.*
Staiano-Coico et al, Human Keratinocyte Growth Factor Effects in a Porcine Model of Epidermal Wound Healing, The Journal of Experimental Medicine, 1993, 178, pp. 865-878.*
Wearing et al, Keratinocyte growth factor signalling: a mathematical model of dermal-epidermal interaction in epidermal wound healing, Mathematical Biosciences, 2000, 165, pp. 41-62.*
Andreadis et al., "Keratinocyte growth factor induces hyperproliferation and delays differentiation in a skin equivalent model system," FASEB J., 15:898-906, 2001.
Curtsinger et al., "Reversal of Adriamycin-impaired wound healing by transforming growth factor-beta," Surgery, Gynecology & Obstetrics, 168(6):517-522, 1989.
Dreher et al., "Temperature Triggered Self-Assembly of Polypeptides into Multivalent Spherical Micelles," JACS Articles— J. Am. Chem. Soc.,130, 687-694, 2008.
Epstein et al, "Therapeutic interventions for enhancing collateral development by administration of growth factors: basic principles, early results and potential hazards," Cardiovascular Res, 49(3): 532-542, 2001.
Geer et al, "Biomimetic delivery of keratinocyte growth factor upon cellular demand for accelerated wound healing in vitro and in vivo," Am J Pathology, 167(6): 1575-1586, 2005.
Huang et al, "Optically responsive gold nanorod-polypeptide assemblies," Langmuir, 24:14139-44, 2008.
Marti et al, "KGF-1 for wound healing in animal models," Meth Mol Biol, 423:383-391, 2008.
McDowall et al., "The role of activins and follistatins in skin and hair follicle development and function," Cytokine & Growth Factor Rev, 19(5-6): 415-426, 2008.
Ron et al., Expression of Biologically Active Recombinant Keratinocyte Growth Factor, The Journal of Biological Chemistry, vol. 268, No. 4, Feb. 5, pp. 2984-2988, 1992.
Shamji et al., "Development and Characterization of a Fusion Protein Between Thermally Responsive Elastin-like Polypeptide and Interleukin-1 Receptor Antagonist," Arthritis & Rheumatism, vol. 56, No. 11, pp. 3650-3661, 2007.
Shamji et al., "Synthesis and Characterization of a Thermally-Responsive Tumor Necrosis Factor Antagonist," Journal of Controlled Release, 129, pp. 179-186, 2008.
Steed, Plastic and Reconstructive Surgery, June, 117(7Suppl):143S-149S, 2006.
Urry, "Physical Chemistry of Biological Free Energy Transduction as Demonstrated by Elastic Protein-Based Polymers," J. Phys. Chem. B., 101, pp. 11007-11028, 1997.
Wu et al., "Fabrication of Elastin-Like Polypeptide Nanoparticles for Drug Delivery by Electrospraying," Biomacromolecules, 10, pp. 19-24, 2009.
Antonicelli et al., "Role of the elastin receptor complex (S-Gal/Cath-A/Neu-1) in skin repair and regeneration,"Wound Rep. Reg., 17:631-638 (2009).
Hashimoto et al., "Development of alginate wound dressings linked with hybrid peptides derived from laminin and elastin," Biomaterials, 25:1407-1414 (2004).

* cited by examiner

*Primary Examiner* — Julie Ha
*Assistant Examiner* — Li Ni Komatsu
(74) *Attorney, Agent, or Firm* — Fish & Richardson P.C.

(57) ABSTRACT

The invention is based on the discovery of a potent growth factor delivery system by creating a fusion polypeptide that includes two portions: (i) keratinocyte growth factor protein, and (ii) an elastin-like peptide. This chimera can be administered directly to a wound site, accelerating recovery.

12 Claims, 11 Drawing Sheets

A)
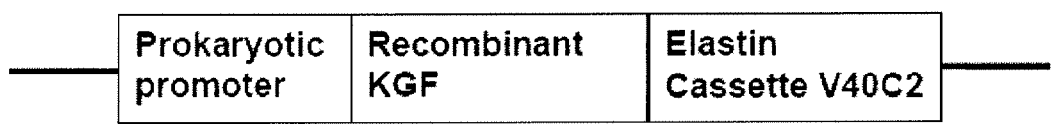
B)
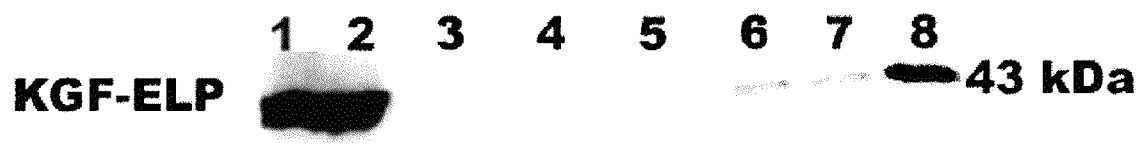
FIGs. 1A-B

A)
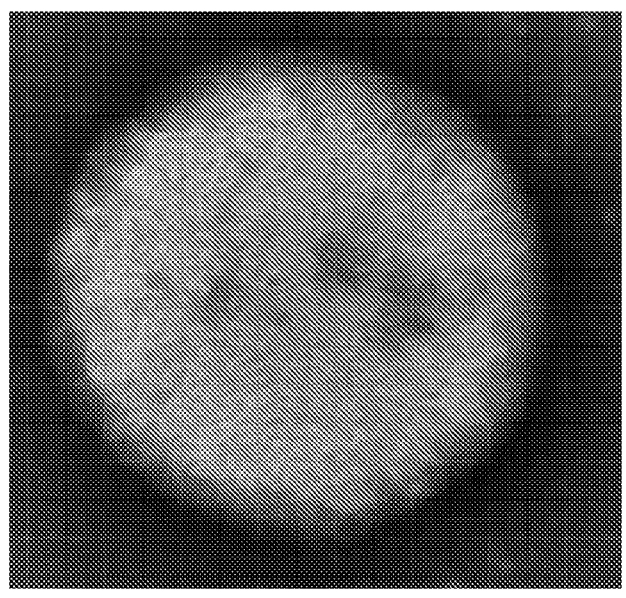
B)
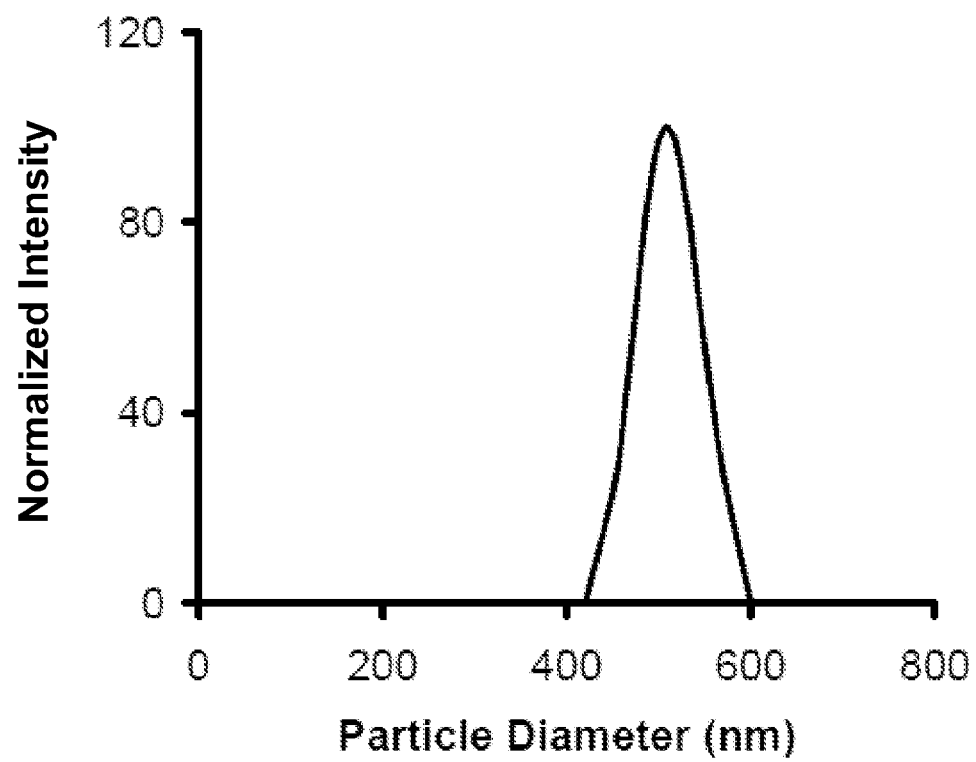
FIGs. 2A-B

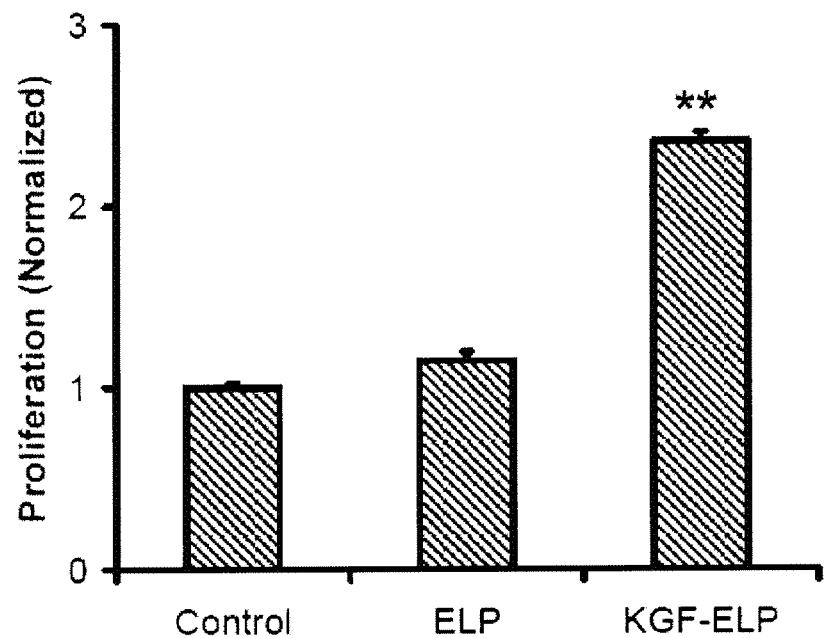
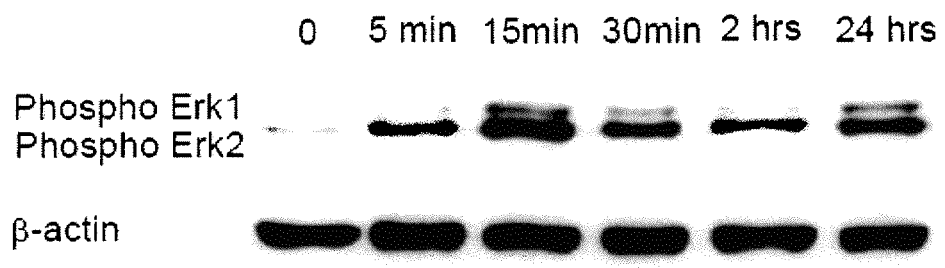
FIGs. 3A-B

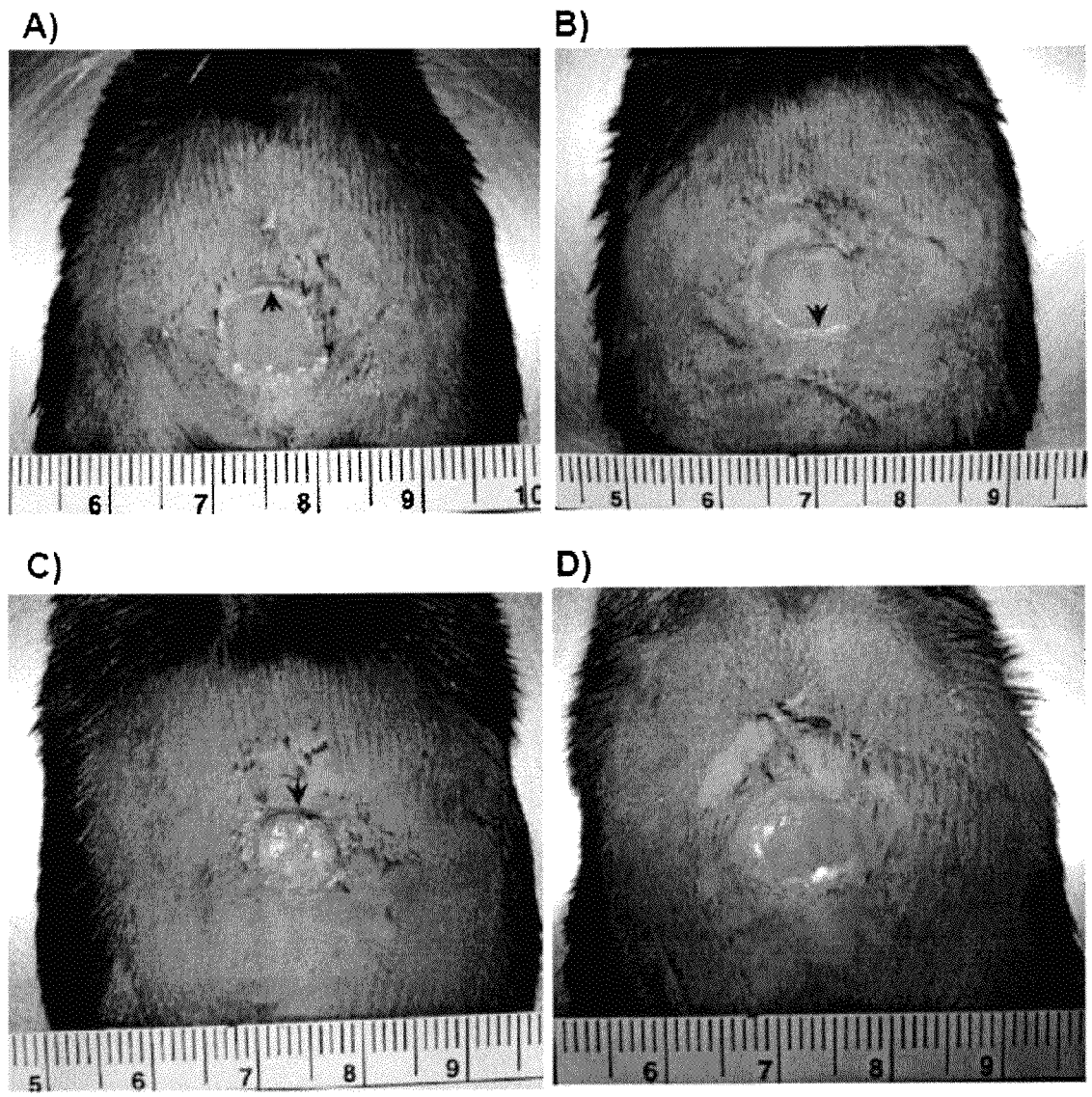
FIGs. 5A-D

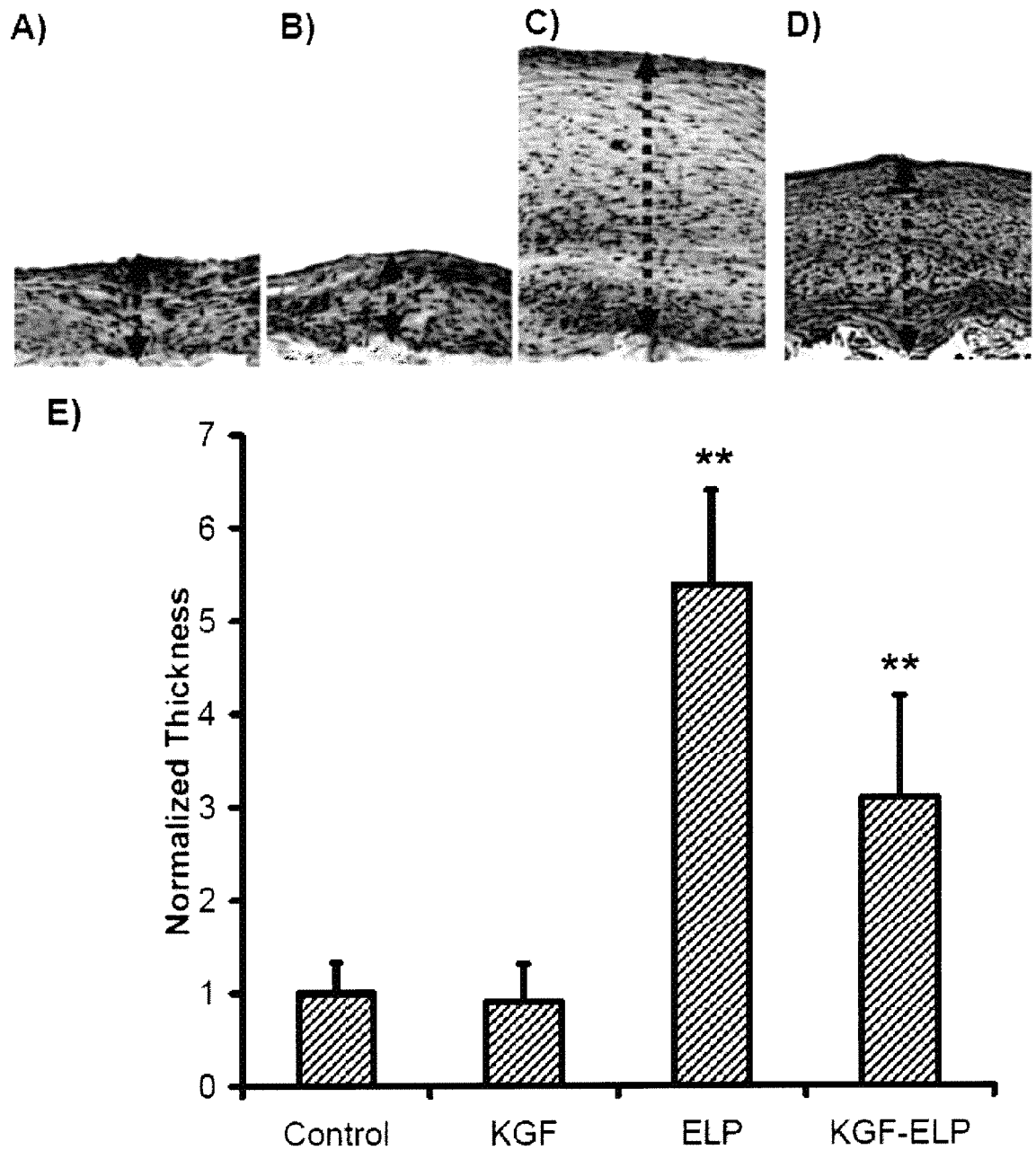
FIGs. 6A-E

A)
B)
FIGs. 7A-B

C)
D)
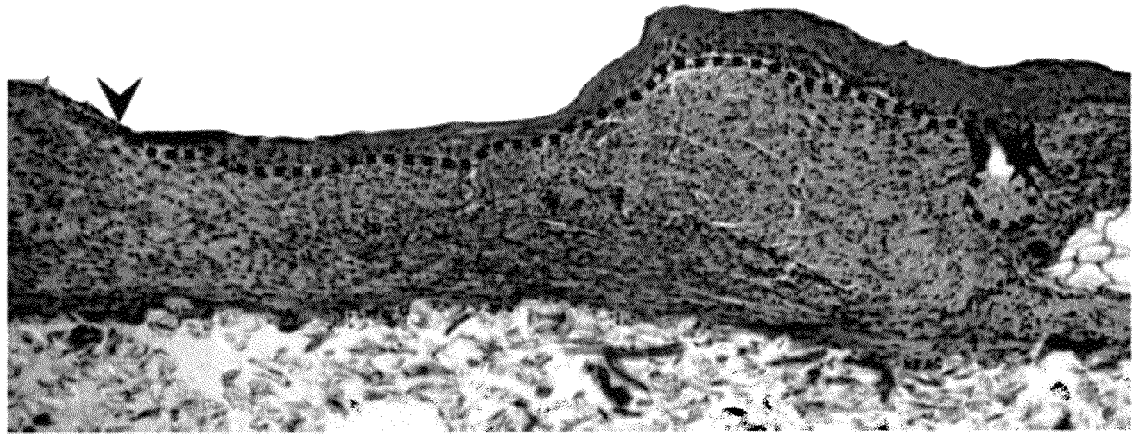
FIGs. 7C-D

SEQUENCE LISTING

```
<160> NUMBER OF SEQ ID NOS: 3

<210> SEQ ID NO 1
<211> LENGTH: 1368
<212> TYPE: DNA
<213> ORGANISM: Artificial Sequence
<220> FEATURE:
<223> OTHER INFORMATION: synthesized in the laboratory

<400> SEQUENCE: 1
atgggccacg gcgtgggtat gcacaaatgg atactgacat ggatcctgcc aactttgctc      60
tacagatcat gctttcacat tatctgtcta gtgggtacta tatctttagc ttgcaatgac     120
atgactccag agcaaatggc tacaaatgtg aactgttcca gccctgagcg acacacaaga     180
```

```
agttatgatt acatggaagg agggatata agagtgagaa gactcttctg tcgaacacag      240
tggtacctga ggatcgataa aagaggcaaa gtaaaaggga cccaagagat gaagaataat      300
tacaatatca tggaaatcag gacagtggca gttggaattg tggcaatcaa aggggtggaa      360
agtgaattct atcttgcaat gaacaaggaa ggaaaactct atgcaaagaa gaatgcaat       420 gaagattgta acttcaaaga actaattctg gaaaaccatt acaacacata tgcatcagct      480
aaatggacac acaacggagg ggaaatgttt gttgccttaa atcaaaaggg gattcctgta      540
agaggaaaaa aaacgaagaa agaacaaaaa acagcccact ttcttcctat ggcaataact      600
tactcgccgg gcgtgggtgt cccaggtgtg ggcgtaccgg gcgttggtgt tcctggtgtc      660
ggcgtgccgg gcgtgggtgt tccgggcgta ggtgtcccag gtgtgggcgt accgggcgtt      720
ggtgttcctg gtgtcggcgt gccgggcgtg gtgttccgg gcgtaggtgt cccaggtgtg      780
ggcgtaccgg gcgttggtgt tcctggtgtc ggcgtgccgg gcgtgggtgt tccgggcgta      840
ggtgtcccag gtgtgggcgt accgggcgtt ggtgttcctg gtgtcggcgt gccgggcgtg      900 gtgttccgg gcgtaggtgt cccaggtgtg ggcgtaccgg gcgttggtgt tcctggtgtc      960
ggcgtgccgg gcgtgggtgt tccgggcgta ggtgtcccag gtgtgggcgt accgggcgtt     1020
ggtgttcctg gtgtcggcgt gccgggcgtg gtgttccgg gcgtaggtgt cccaggtgtg     1080
ggcgtaccgg gcgttggtgt tcctggtgtc ggcgtgccgg gcgtgggtgt tccgggcgta     1140
ggtgtcccag gtgtgggcgt accgggcgtt ggtgttcctg gtgtcggcgt gccgggcgtg     1200
ggtgttccgg gcgtaggtgt cccaggtgtg gcgtaccgg gcgttggtgt tcctggttgc      1260
ggcgtgccgg gcgtgggtgt tccgggcgta ggtgtcccag gtgtgggcgt accgggcgtt     1320
ggtgttcctg gttgcggcgt gccgggcgtg ggtgttccgg gcgtaggt                  1368
```

<210> SEQ ID NO 2
<211> LENGTH: 456
<212> TYPE: PRT
<213> ORGANISM: Artificial Sequence
<220> FEATURE:
<223> OTHER INFORMATION: synthesized in the laboratory

<400> SEQUENCE: 2

```
Met Gly His Gly Val Gly Met His Lys Trp Ile Leu Thr Trp Ile Leu
1               5                   10                  15

Pro Thr Leu Leu Tyr Arg Ser Cys Phe His Ile Ile Cys Leu Val Gly
            20                  25                  30

Thr Ile Ser Leu Ala Cys Asn Asp Met Thr Pro Glu Gln Met Ala Thr
        35                  40                  45

Asn Val Asn Cys Ser Ser Pro Glu Arg His Thr Arg Ser Tyr Asp Tyr
    50                  55                  60

Met Glu Gly Gly Asp Ile Arg Val Arg Arg Leu Phe Cys Arg Thr Gln
65                  70                  75                  80

Trp Tyr Leu Arg Ile Asp Lys Arg Gly Lys Val Lys Gly Thr Gln Glu
                85                  90                  95

Met Lys Asn Asn Tyr Asn Ile Met Glu Ile Arg Thr Val Ala Val Gly
            100                 105                 110

Ile Val Ala Ile Lys Gly Val Glu Ser Glu Phe Tyr Leu Ala Met Asn
        115                 120                 125

Lys Glu Gly Lys Leu Tyr Ala Lys Lys Glu Cys Asn Glu Asp Cys Asn
    130                 135                 140

Phe Lys Glu Leu Ile Leu Glu Asn His Tyr Asn Thr Tyr Ala Ser Ala
145                 150                 155                 160
```

-continued

```
Lys Trp Thr His Asn Gly Gly Glu Met Phe Val Ala Leu Asn Gln Lys
                165                 170                 175
Gly Ile Pro Val Arg Gly Lys Lys Thr Lys Lys Glu Gln Lys Thr Ala
            180                 185                 190
His Phe Leu Pro Met Ala Ile Thr Tyr Ser Pro Gly Val Gly Val Pro
        195                 200                 205
Gly Val Gly Val Pro Gly Val Gly Val Pro Gly Val Gly Val Pro Gly
    210                 215                 220
Val Gly Val Pro Gly Val Gly Val Pro Gly Val Gly Val Pro Gly Val
225                 230                 235                 240
Gly Val Pro Gly Val Gly Val Pro Gly Val Gly Val Pro Gly Val Gly
            245                 250                 255
Val Pro Gly Val Gly Val Pro Gly Val Gly Val Pro Gly Val Gly Val
        260                 265                 270
Pro Gly Val Gly Val Pro Gly Val Gly Val Pro Gly Val Gly Val Pro
    275                 280                 285
Gly Val Gly Val Pro Gly Val Gly Val Pro Gly Val Gly Val Pro Gly
    290                 295                 300
Val Gly Val Pro Gly Val Gly Val Pro Gly Val Gly Val Pro Gly Val
305                 310                 315                 320
Gly Val Pro Gly Val Gly Val Pro Gly Val Gly Val Pro Gly Val Gly
            325                 330                 335
Val Pro Gly Val Gly Val Pro Gly Val Gly Val Pro Gly Val Gly Val
        340                 345                 350
Pro Gly Val Gly Val Pro Gly Val Gly Val Pro Gly Val Gly Val Pro
    355                 360                 365
Gly Val Gly Val Pro Gly Val Gly Val Pro Gly Val Gly Val Pro Gly
    370                 375                 380
Val Gly Val Pro Gly Val Gly Val Pro Gly Val Gly Val Pro Gly Val
385                 390                 395                 400
Gly Val Pro Gly Val Gly Val Pro Gly Val Gly Val Pro Gly Val Gly
            405                 410                 415
Val Pro Gly Cys Gly Val Pro Gly Val Gly Val Pro Gly Val Gly Val
        420                 425                 430
Pro Gly Val Gly Val Pro Gly Val Gly Val Pro Gly Cys Gly Val Pro
    435                 440                 445
Gly Val Gly Val Pro Gly Val Gly
    450                 455

<210> SEQ ID NO 3
<211> LENGTH: 6
<212> TYPE: PRT
<213> ORGANISM: Artificial Sequence
<220> FEATURE:
<223> OTHER INFORMATION: linker sequence

<400> SEQUENCE: 3

Tyr Ser Pro Gly Val Gly
1               5
```

ELASTIN BASED GROWTH FACTOR DELIVERY PLATFORM FOR WOUND HEALING AND REGENERATION

CROSS REFERENCE TO RELATED APPLICATIONS

This application claims the benefit of U.S. Application No. 61/249,682, filed on Oct. 8, 2009, the entire contents of which are hereby incorporated by reference.

FEDERALLY SPONSORED RESEARCH OR DEVELOPMENT

This invention was made with Government support under Grant Numbers EB002503 awarded by the National Institutes of Health and W81XWH-07-1-0302 awarded by the ARMY/Department of Defense. The Government has certain rights in the invention.

TECHNICAL FIELD

This invention relates to a growth factor delivery platform based on elastin-like peptides, which is useful in treating wounds, e.g., burns, ulcers.

BACKGROUND

A staggering one million burn injuries occur in the United States every year and over 45,000 require hospitalization. Severe extensive burns covering over 60% of the total body surface area account for 4% of the admissions, about 2,000 patients per year. Burn injuries are especially common among children, with nearly 80,000 infants being treated annually, making burns the third leading cause of childhood injury-related mortality in both Canada and the United States (Hammig and Ogletree (2006) Am J Health Behav 30:259-267). Second and third degree burns cause severe damage to the skin dermal layer.

Epidermal regeneration is a complex process in which keratinocytes proliferate and migrate to cover up the defect in the epidermis restoring lost barrier function of the skin. The molecular mechanisms involved in this process are still not completely understood but peptide growth factors, e.g., keratinocyte growth factor (KGF), have been shown to play an important role in epidermal regeneration (Hardwicke et al. (2008) Surgeon 6(3):172-177; McDowall et al. (2008) Cytokine & Growth Factor Rev 19(5-6):415-426; Koria and Andreadis (2007) Am J Phys 293(3):C1020-1031; Werner and Grose (2003) Physiological Rev 83(3):835-870; Grazul-Bilska et al. (2003) Drugs Today (Bare) 39(10):787-800; Curtsinger et al. (1989) Surgery, Gynecology & Obstetrics 168(6):517-522; Brown et al. (1986) J Exp Med 163(5):1319-1324).

KGF is a monomeric peptide belonging to the fibroblast growth factor family (FGF-7) and plays a prominent role in epidermal morphogenesis and wound healing (Werner et al. (1994) Science 266(5186):819-822; Beer et al. (2000) J Investigative Dermatol Symp Proc 5(1):34-39). It is mainly expressed by cells of mesenchymal origin such as fibroblasts, micro-vascular endothelial and smooth muscle cells but affects epithelial cells (Winkles et al. (1997) J Cell Physiol 173(3):380-386; Smola et al. (1993) J Cell Biol 122(2):417-429). This paracrine mode of action of KGF on epithelial cells is mediated through the KGF receptor (KGFR or FGFRIIIb), a splice variant of the FGF-2 receptor encoded by the gene fgfr-2 (Mild et al. (1991) Science 251(4989):72-75; Miki et al. (1992) Proc Natl Acad Sci USA 89(1):246-250). KGF is present at very low levels in skin under normal conditions but it is highly up-regulated after injury (Werner et al. (1992) Proc Natl Acad Sci USA 89(15):6896-6900). While wound healing of KGFR deficient mice was severely impaired (Werner et al. (1994) Science 266(5186):819-822), mice lacking KGF healed at normal rates (Guo et al. (1996) Genes Dev 10(2): 165-175), possibly due to the compensatory action by other members of the FGF family e.g. FGF-10 (Beer et al. (1997) Oncogene 15(18):2211-2218) or FGF-22 (Beyer et al. (2003) Exp Cell Res 287(2):228-236). Despite such redundancies exogenous KGF significantly enhanced re-epithelialization of full and partial thickness wounds in porcine and rabbit ear wound models (Staiano-Coico et al. (1993) J Exp Med 178 (3):865-878; Pierce et al. (1994) J Exp Med 179(3):831-840). In addition to re-epithelialization, exogenous delivery of KGF enhanced granulation tissue formation in an ischemic rabbit ear wound model (Gillis et al. (1999) J Cell Sci 112(Pt 12):2049-2057) and injection of KGF DNA accelerated wound closure and reduced inflammation in a diabetic mouse model (Marti et al. (2004) Gene Ther 2004 11(24):1780-1785). Furthermore, development of engineered skin equivalents with KGF-expressing human keratinocytes showed changes in epidermal structure and morphology including hyper-thickening (Andreadis et al. (2001) FASEB J 15(6): 898-906).

Initial clinical studies on topical application of growth factor preparations to accelerate epidermal regeneration gave controversial results (Brown et al. (1991) Plastic Reconstructive Surgery 88(2):189-194; discussion 195-186; Brown et al. (1988) Annals Surgery 208(6):788-794; Brown et al. (1989) New England J Med 321(2):76-79). This was largely due to the limited bioavailability of topically delivered growth factors in the wound environment (Curtsinger et al. (1989) Surgery, Gynecology & Obstetrics 168(6):517-522; Brown et al. (1989) New England J Med 321(2):76-79). Such topical treatment does not keep the growth factor localized in the wound and necessitates the use of large amounts of growth factor (Marti et al. (2008) Meth Mol Biol 423:383-391). This is not only associated with high cost but also potential side effects such as vascularization of non target tissues or tumors (Epstein et al. (2001) Cardiovascular Res 49(3):532-542). Therefore, there is a need to design growth factor delivery systems that ensure presence of the growth factor during the epidermal regeneration process. Several groups have devised strategies to address this issue. Current strategies include chemical conjugation of growth factors to extra-cellular molecules like fibrin or collagen (Geer et al. (2005) Am J Pathology 167(6): 1575-1586; Curtsinger et al. (1989) Surgery, Gynecology & Obstetrics 168(6):517-522), delivery vehicles like multi-lamellar vesicles (Brown et al. (1988) Annals Surgery 208(6): 788-794) or gene therapy which involves delivery of a growth factor encoding plasmid to the target cells (Davidson (2008) J Invest Derm 128(6):1360-1362; Escamez et al. (2008) J Invest Derm 128(6):1565-1575; Hirsch et al. (2007) Front Biosci 12:2507-2518), or transplanting genetically modified cells that over-express KGF (Kopp et al. (2004) Mol Ther 10(1):86-96). Chemical conjugation of growth factors requires large quantities of the growth factor, increasing the cost of treatment. While gene therapy has proven effective in some cases, several extra cellular and intracellular barriers must be overcome in order to obtain successful expression of the transgene (Hirsch et al. (2007) Front Biosci 12:2507-2518). Moreover, once these barriers have been successfully overcome, there is generally little control over the duration of expression or amount of growth factor produced by the transfected cell (Yao and Eriksson (2000) Wound Repair Regen 8(6):443-451; Byrnes et al. (1997) J Phys Chem B 101(51): 11007-11028). Furthermore, in instances where the delivery of multiple growth factors is desired, the recalcitrance of some transfected cells to further transfections may be an issue. Therefore, there is a great demand for devising strategies that improve and accelerate the process of wound healing.

SUMMARY

The present invention is based, at least in part, on the discovery that one can produce a growth factor delivery system by creating a purified fusion polypeptide (chimera) that comprises a keratinocyte growth factor (KGF) and an elastin-like peptide (ELP). This fusion polypeptide retains the bioactivity of recombinant KGF as well as the characteristic ELP inverse phase transitioning behavior. Furthermore, the inverse phase transitioning behavior of ELP promotes the formation of aggregating particles (diameter=500 nm) at temperatures greater than 30° C. These particles are stable over a range of temperatures (30° C. to 60° C.) and improve growth of A431 cells as well as wound healing both in vivo and in vitro. The particles are internalized in the keratinocytes, a process that is dependent on the KGF receptor. These characteristics combined make them unique to other elastin-like particles such as U.S. Patent Pub. No. 2007/0265197 A1.

In one aspect, the invention features a purified polypeptide that comprises at least two portions: (i) a KGF monomer, e.g., a FGF7 protein, which is recognized by the KGF receptor, a splice variant of the FGF-2 receptor encoded by the gene fgfr-2, and (ii) an elastin-like peptide (ELP) having an amino acid sequence comprising $(VPGXG)_{47-101}$, where $X \neq Pro$, e.g., $V_nC_y$, where V=VPGXG, C=$(VPGXG)_{2-5}$ VPGCG $(VPGXG)_{2-5}$, $X \neq Pro$, n=37-46, and y=2-5; and $V_{40}C_2$, where V=VPGVG and C=$(VPGVG)_2$ VPGCG $(VPGVG)_2$. In some embodiments, the KGF comprises an amino acid sequence that is at least 95% (e.g., 96%, 97%, 98%, 99%, or 100%) identical to amino acids 7-200 of SEQ ID NO:2. In one embodiment, the ELP comprises an amino acid sequence that is at least 95% (e.g., 96%, 97%, 98%, 99%, or 100%) identical to amino acids 207-456 of SEQ ID NO:2. In one embodiment, the polypeptide comprises an amino acid sequence that is at least 95% (e.g., 96%, 97%, 98%, 99%, or 100%) identical to SEQ ID NO:2. In some embodiments, the polypeptides include a third linker sequence between KGF and ELP. These polypeptides can be administered directly to wound sites to accelerate healing.

In another aspect, the invention provides isolated nucleic acid molecules that encode one or more of the fusion polypeptides. In one embodiment, the nucleic acid molecule comprises a nucleic acid sequence that encodes a fusion polypeptide comprising a KGF linked to an ELP having an amino acid sequence comprising $(VPGXG)_{47-101}$, where $X \neq Pro$. In one embodiment, the KGF is encoded by a nucleic acid sequence that is at least 95% (e.g., 96%, 97%, 98%, 99%, or 100%) identical to nucleotides 19-600 of SEQ ID NO:1. In one embodiment, the ELP is encoded by a nucleic acid sequence that is at least 95% identical to nucleotides 619-1368 of SEQ ID NO:1. In one embodiment, the nucleic acid molecule comprises a nucleotide sequence that is at least 95% (e.g., 96%, 97%, 98%, 99%, or 100%) identical to SEQ ID NO:1. The nucleic acid molecule may be in a nucleic acid vector, which can be within a cell.

The invention also provides methods of treating a subject who has a wound (e.g., burn, ulcer), the method comprising selecting a subject and administering a therapeutically effective amount of a composition comprising a fusion polypeptide comprising KGF linked to ELP. In one embodiment, the composition (e.g., polymer) comprises a plurality of the fusion polypeptides described herein. In use, the fusion polypeptides automatically form polymers in solution between 30-60° C. In another embodiment, the invention features methods of delivering the fusion polypeptide to target cells, e.g., injection, irrigation, infusion, continuous infusion, topical formulation (e.g., cream or gel).

The term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded.

The term "isolated" or "purified," when applied to a nucleic acid molecule, includes nucleic acid molecules that are separated from other materials, including other nucleic acids, which are present in the natural source of the nucleic acid molecule. For example, with respect to genomic DNA, the term "isolated" includes nucleic acid molecules that are separated from the chromosome with which the genomic DNA is naturally associated. In some embodiments, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that the preparation of a selected protein (e.g., KGF-ELP fusion polypeptide) has less than about 30% (e.g., less than 20%, 10%, or 5%) by dry weight, of non-selected protein or of chemical precursors (e.g., a protein other than KGF-ELP polypeptide). Such a non-selected protein is also referred to herein as a "contaminating protein." When the KGF-ELP polypeptide is recombinantly produced, it is also preferably substantially free of culture medium, i.e., culture medium represents less than about 20%, (e.g., less than about 10% or 5%) of the volume of the protein preparation. The invention includes isolated or purified preparations of at least 0.01, 0.1, 1.0, and 10 milligrams in dry weight.

"Subject," as used herein, is an animal such as a mammal, e.g., an experimental animal such as a burn model, or a human. The subject can also be a non-human animal, e.g., a horse, cow, goat, or other domestic animal. In some embodiments, the subject is diabetic.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-B. Preparation of the fusion peptide. FIG. 1A is a schematic diagram of recombinant KGF cloned in front of the elastin cassette $V_{40}C_2$, as described in Example 1. FIG. 1B is a photograph of a Western blot for detecting KGF using an anti-KGF antibody in various samples. Lanes 1 and 2—Bacterial cell lysate; Lane 3—Supernatant after first hot spin; Lane 4—Supernatant after second hot spin; Lane 5—Supernatant after third hot spin; Lane 6—Pellet after first re-suspension; Lane 7—Pellet after second re-suspension; Lane 8—Lyophilized KGF-ELP re-suspended in phosphate buffered saline.

FIGS. 2A-C. Formation of particles. FIG. 2A is a TEM image of the formed KGF-ELP particles. The KGF-ELP was dissolved in deionized water and incubated at 37° C. to initiate particle formation. These particles were stained and then imaged using TEM. Bar=100 nm. FIG. 2B is a line graph showing particle size distribution of the formed KGF-ELP particles. The elastin fusion peptide was dissolved in PBS and particle size was determined as described in Example 2. FIG. 2C is a scatter plot showing particle diameter as a function of temperature. The fusion peptide was dissolved in PBS and then determination of particle size was done by incubating the solution at the indicated temperatures. At temperatures lower then the transition temperature, the fusion peptide exists as a monomer. As the temperature is increased over 30° C., the elastin chains come together to form submicron-sized particles.

FIGS. 3A-C. KGF-ELP fusion retains the biological activity of KGF and ELP. FIG. 3A is a bar graph showing the amount of proliferation induced by various treatments on keratinocytes. Keratinocytes were serum starved overnight and the next day, were treated with either serum-free DMEM (control), KGF-ELP fusion protein (10 µg/mL), or ELPs (10 µg/mL). After two days, cell numbers were assessed by Hoechst assay and normalized to the control cell number (y axis). This experiment was repeated two times with triplicates and a representative experiment is shown. indicates p<0.05 when compared to control. FIG. 3B is a photograph of a Western blot showing that KGF-ELP phosphorylates ERK1 and ERK2 in cultured keratinocytes. Keratinocytes were serum-starved overnight and then treated with KGF-ELP (10 µg/mL) for the indicated times. The cells were then lysed and the lysates were subjected to Western blot using an antibody specific to phosphorylated ERK1 and ERK2. For loading control, the blots were stripped and re-probed for β-actin. FIG. 3C is a bar graph showing the amount of proliferation induced by various treatments on fibroblasts. Fibroblasts were serum-starved overnight and the next day, were treated with either serum-free DMEM (control), KGF-ELP fusion protein (10 µg/mL), or ELPs (10 µg/mL). After two days, cell numbers were assessed by Hoechst assay and normalized to the control cell number (y axis). This experiment was repeated two times with triplicates and a representative experiment is shown. indicates p<0.05 when compared to control.

FIGS. 5A-D is a series of four photographs showing that KGF-ELP particles improve wound healing in genetically diabetic mice. Full thickness wounds were created on the back of genetically diabetic mice. Gross morphology of the wounds treated with either Fibrin gel (FIG. 5A), Fibrin gel containing KGF (FIG. 5B), Fibrin gel containing elastin particles (FIG. 5C), or Fibrin gel containing KGF-ELP particles (FIG. 5D). See arrowhead for edge of the wound.

FIGS. 6A-E is a series of four photographs and a bar graph showing that elastin enhances granulation tissue of full thickness wounds in genetically diabetic mice. Full thickness wounds were created on the back of genetically diabetic mice. The mice were then treated with either Fibrin gel (FIG. 6A), Fibrin gel containing KGF (FIG. 6B), Fibrin gel containing elastin particles (FIG. 6C), or Fibrin gel containing KGF-ELP particles (FIG. 6D). The figure shows the middle of the wound after 14 days. The dotted arrow in the middle of the wounds was quantified. Bar=400 µm. FIG. 6E is a bar graph showing the thickness of granulation tissue for each of the four treatments. Each value represents the mean thickness from 7 mice (n=7). **=p<0.05 when compared to control or KGF.

FIGS. 7A-E is a series of four photographs and a bar graph showing that KGF-ELP enhances re-epithelialization in full thickness wounds in diabetic mice. Full thickness wounds were created on the back of genetically diabetic mice. The mice were then treated with either Fibrin gel (FIG. 7A), Fibrin gel containing KGF (FIG. 7B), Fibrin gel containing elastin particles (FIG. 7C), or Fibrin gel containing KGF-ELP particles (FIG. 7D). The wounded animals were sacrificed after 14 days; the tissue was harvested and stained with Hematoxylin and Eosin. The up arrow indicates the edge of the created wound and the down arrow indicates the tip of the migrating tongue of the wound. Dotted line represents the extent of re-epithelialization. Bar=400 µm. FIG. 7E is a bar graph showing the amount of re-epithelialization for each of the four treatments. Each bar represents the length of migration (dotted line) normalized to the control (Fibrin Gel treatment). The value is representative of a mean of 7 animals for each group (n=7). **=p<0.05 when compared to control, KGF, and elastin.

DETAILED DESCRIPTION

Figure 2C:
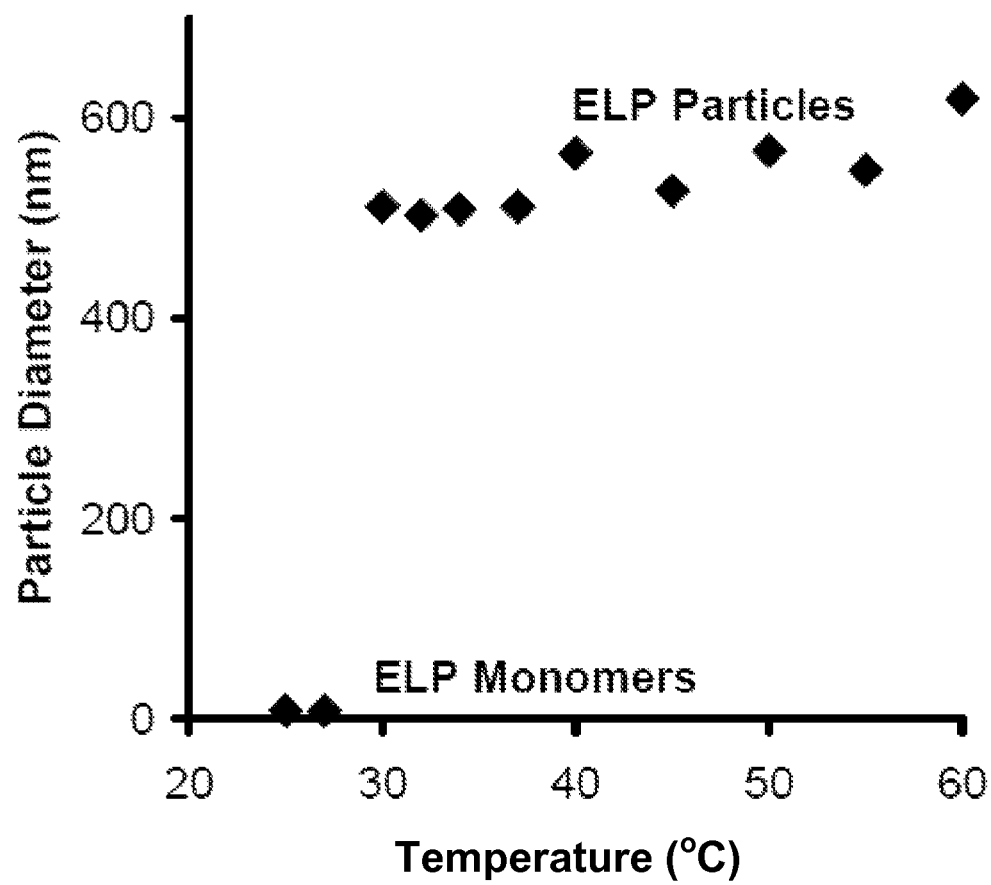

One strategy to improve wound healing is the delivery of growth factors like keratinocyte growth factor (KGF) locally to the wound. KGF is not expressed in normal skin, but its expression is highly up-regulated during wound healing. It is one of the most potent mitogens of epithelial cells. Studies involving several in vivo models have shown its efficacy in wound healing. Despite these efforts, there is still a lack of robust delivery methods for KGF. Existing approaches include bullous delivery of KGF to the wounds or gene therapy approaches. Gene therapy is associated with significant dangers. The addition of KGF in saline solutions has limited utility because of its rapid clearance and short half life in the harsh wound environment. Therefore, there is a requirement of devising drug delivery platforms that ensure a constant release of the growth factor at the wound site during the whole regeneration process.

Here, a growth factor delivery platform based on elastin-like polypeptides (ELPs) is described. In one embodiment, the fusion protein comprises KGF and ELP. This fusion protein retains the characteristic ELP inverse phase transitioning behavior as well as the bioactivity of recombinant KGF. Furthermore, the inverse phase transitioning behavior of ELP promotes the formation of aggregating particles at physiological temperature displaying KGF at their periphery. This elastin-based delivery platform can be used effectively to improve healing of wounds.

In general, the compositions described herein include nucleic acid molecules including a nucleotide sequence that fuses a cDNA for a growth factor, e.g., KGF, in frame with a gene encoding ELP cassette $V_{40}C_2$ and/or polypeptides comprising a growth factor, e.g., KGF, linked to ELP cassette $V_{40}C_2$. The polypeptide can be synthesized and linked, e.g., chemically, but is typically generated using standard recombinant genetic engineering techniques.

Keratinocyte Growth Factor (KGF)

Keratinocyte Growth Factor, encoded by FGF7, is a member of the fibroblast growth factor (FGF) family. FGF family members possess broad mitogenic and cell survival activities and are involved in a variety of biological processes, including embryonic development, cell growth, morphogenesis, tissue repair, tumor growth and invasion. This protein is a potent epithelial cell-specific growth factor, whose mitogenic activity is predominantly exhibited in keratinocytes. FGF7 stimulates the repair of injured skin and mucosal tissues by stimulating the proliferation, migration and differentiation of epithelial cells, and they have direct chemotactic effects on tissue remodeling. Some examples of FGF7 are highlighted below in Table 1, and substantially identical nucleotide sequences can also be used. As used herein, "substantially identical" refers to a nucleotide sequence that contains a sufficient or minimum number of identical or equivalent nucleotides to the sequence of FGF7, such that homologous recombination can occur. For example, nucleotide sequences that are at least about 75% identical to the sequence of FGF7 are defined herein as substantially identical. In some embodiments, the nucleotide sequences are about 80%, 85%, 90%, 95%, 96%, 97%, 98%, 99%, or 100% identical.

TABLE 1

Keratinocyte growth factor orthologs from seven different species along with their GenBank Ref Seq Accession Numbers.

| Species | Nucleic Acid | Amino Acid | GeneID |
|---|---|---|---|
| Homo sapiens | NM_002009.3 | NP_002000.1 | 2252 |
| Mus musculus | NM_008008.3 | NP_032034.1 | 14178 |
| Rattus norvegicus | NM_022182.1 | NP_071518.1 | 29348 |
| Canis lupus familiaris | NM_001003237.1 | NP_001003237.1 | 403915 |
| Macaca mulatta | NC_007864.1 | NW_001121152.1 | 574345 |
| Ovis aries | NM_001009235.1 | NP_001009235.1 | 443095 |
| Gallus gallus | NM_001012525.1 | NP_001012543.1 | 415439 |

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, 96%, 97%, 98%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Elastin-Like Polypeptides (ELPs)

Elastin-like polypeptides (ELPs) are biocompatible, non-immunogenic polymers composed of tandemly-repeated blocks of (Val-Pro-Gly-X-Gly)$_N$, where X is any residue but Pro (Urry (1997) J Phys Chem B 101(51):11007-11028; Chilkoti et al. (2002) Adv Drug Delivery Rev 54(8):1093-1111). This sequence motif is derived from the hydrophobic domain of tropoelastin. At temperatures below an inverse transition temperature ($T_t$; also known as a lower critical solution temperature (LCST)), ELPs are soluble in aqueous solutions. However as the temperature is raised above the $T_t$, ELPs undergo an entropically-driven, temperature-induced contraction and self assembly, rendering them insoluble. This property enables recombinant ELPs to be rapidly purified to high homogeneity from bacterial lysate using inverse temperature cycling (ITC) (Meyer and Chilkoti (1999) Nat Biotechnol 17(11):1112-1115).

KGF-ELP

Exemplary KGF-ELP fusion nucleotide and protein sequences are listed below. The regular italicized font indicates leading sequence immediately preceding the KGF domain (regular font). A linker comprising 18 nucleotides or 6 amino acids is indicated by the underlined font, followed immediately by the ELP domain in bold font.

KGF-ELP Nucleic acid Sequence (SEQ ID NO: 1)

*ATGGGCCACGGCGTGGG*TATGCACAAATGGATACTGACATGGATCCTG

CCAACTTTGCTCTACAGATCATGCTTTCACATTATCTGTCTAGTGGGT

ACTATATCTTTAGCTTGCAATGACATGACTCCAGAGCAAATGGCTACA

AATGTGAACTGTTCCAGCCCTGAGCGACACACAAGAAGTTATGATTAC

ATGGAAGGAGGGGATATAAGAGTGAGAAGACTCTTCTGTCGAACACAG

TGGTACCTGAGGATCGATAAAAGAGGCAAAGTAAAAGGGACCCAAGAG

ATGAAGAATAATTACAATATCATGGAAATCAGGACAGTGGCAGTTGGA

ATTGTGGCAATCAAAGGGGTGGAAAGTGAATTCTATCTTGCAATGAAC

AAGGAAGGAAAACTCTATGCAAAGAAAGAATGCAATGAAGATTGTAAC

TTCAAAGAACTAATTCTGGAAAACCATTACAACACATATGCATCAGCT

AAATGGACACACAACGGAGGGGAAATGTTTGTTGCCTTAAATCAAAAG

GGGATTCCTGTAAGAGGAAAAAAAACGAAGAAAGAACAAAAAACAGCC

CACTTTCTTCCTATGGCAATAACT<u>TACTCGCCGGGCGTGGG</u>GTCCCA

GGTGTGGGCGTACCGGGCGTTGGTGTTCCTGGTGTCGGCGTGCCGGGC

```
-continued
GTGGGTGTTCCGGGCGTAGGTGTCCCAGGTGTGGGCGTACCGGGCGTT

GGTGTTCCTGGTGTCGGCGTGCCGGGCGTGGGTGTTCCGGGCGTAGGT

GTCCCAGGTGTGGGCGTACCGGGCGTTGGTGTTCCTGGTGTCGGCGTG

CCGGGCGTGGGTGTTCCGGGCGTAGGTGTCCCAGGTGTGGGCGTACCG

GGCGTTGGTGTTCCTGGTGTCGGCGTGCCGGGCGTGGGTGTTCCGGGC

GTAGGTGTCCCAGGTGTGGGCGTACCGGGCGTTGGTGTTCCTGGTGTC

GGCGTGCCGGGCGTGGGTGTTCCGGGCGTAGGTGTCCCAGGTGTGGGC

GTACCGGGCGTTGGTGTTCCTGGTGTCGGCGTGCCGGGCGTGGGTGTT

CCGGGCGTAGGTGTCCCAGGTGTGGGCGTACCGGGCGTTGGTGTTCCT

GGTGTCGGCGTGCCGGGCGTGGGTGTTCCGGGCGTAGGTGTCCCAGGT

GTGGGCGTACCGGGCGTTGGTGTTCCTGGTGTCGGCGTGCCGGGCGTG

GGTGTTCCGGGCGTAGGTGTCCCAGGTGTGGGCGTACCGGGCGTTGGT

GTTCCTGGTTGCGGCGTGCCGGGCGTGGGTGTTCCGGGCGTAGGTGTC

CCAGGTGTGGGCGTACCGGGCGTTGGTGTTCCTGGTTGCGGCGTGCCG

GGCGTGGGTGTTCCGGGCGTAGGT

KGF-ELP Protein Sequence
                                              (SEQ ID NO: 2)
MGHGVGMHKWILTWILPTLLYRSCFHIICLVGTISLACNDMTPEQMAT

NVNCSSPERHTRSYDYMEGGDIRVRRLFCRTQWYLRIDKRGKVKGTQE

MKNNYNIMEIRTVAVGIVAIKGVESEFYLAMNKEGKLYAKKECNEDCN

FKELILENHYNTYASAKWTHNGGEMFVALNQKGIPVRGKKTKKEQKTA

HFLPMAITYSPGVGVPGVGVPGVGVPGVGVPGVGVPGVGVPGVGVPGV

GVPGVGVPGVGVPGVGVPGVGVPGVGVPGVGVPGVGVPGVGVPGVGVP

GVGVPGVGVPGVGVPGVGVPGVGVPGVGVPGVGVPGVGVPGVGVPGVG

VPGVGVPGVGVPGVGVPGVGVPGVGVPGVGVPGVGVPGVGVPGVGVPG

VGVPGVGVPGVGVPGVGVPGVGVPGVGVPGVGVPGCGVPGVGVPGVGV

PGVGVPGVGVPGCGVPGVGVPGVG
```

Recombinant Expression Vectors, Host Cells, and Genetically Engineered Cells

The invention includes vectors, preferably expression vectors, containing a nucleic acid that encodes the chimeras described herein. As used herein, the term "vector" refers to a nucleic acid molecule capable of transporting another nucleic acid to which it has been linked and can include, e.g., a plasmid, cosmid, or viral vector. The vector can autonomously replicate or it can integrate into a host cell's DNA. Viral vectors include, e.g., replication-defective retroviruses, adenoviruses, and adeno-associated viruses.

A vector can include a KGF-ELP nucleic acid in a form suitable for expression of the nucleic acid in a host cell. Preferably a recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce KGF-ELP polypeptides encoded by nucleic acids as described herein.

The recombinant expression vectors of the invention can be designed for expression of KGF-ELP polypeptides in prokaryotic or eukaryotic cells. For example, polypeptides of the invention can be expressed in *E. coli*, insect cells (e.g., using baculovirus expression vectors), yeast cells, or mammalian cells (e.g., CHO or COS cells). Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene, 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

One can maximize recombinant protein expression in *E. coli* by expressing the protein in host bacteria with an impaired capacity to proteolytically cleave the recombinant protein (Gottesman (1990) Gene Expression Technology: Methods in Enzymology 185:119-128, Academic Press, San Diego, Calif.). Another strategy is to alter the nucleic acid sequence of the nucleic acid to be inserted into an expression vector so that the individual codons for each amino acid are those preferentially utilized in *E. coli* (Wada et al. (1992) Nucleic Acids Res 20:2111-2118). Such alteration of nucleic acid sequences of the invention can be carried out by standard DNA synthesis techniques.

Nucleic acids disclosed herein also include both RNA and DNA, including genomic DNA and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

Modified versions of peptides disclosed herein are referred to as "peptide derivatives," and they can also be used in the new methods. For example, peptide derivatives of a peptide can be used instead of that peptide in therapeutic methods described herein. Peptides disclosed herein can be modified according to the methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al. (2003) J. Biol. Chem. 278:45746. In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetic include replacing one or more amino acid residues in a peptide with a chemically distinct but recognized functional analog of the amino acid, i.e., an artificial amino acid analog. Artificial amino acid analogs include β-amino acids, (β-substituted β-amino acids ("β$^3$-amino acids"), phosphorous analogs of amino acids, such as α-amino phosphonic acids and α-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules.

Also provided herein are host cells that include a nucleic acid molecule described herein, e.g., a KGF-ELP nucleic acid molecule, within a recombinant expression vector. This can be accomplished using any of the vectors known in the art or described herein, e.g., a lentiviral vector such as described in Lois et al. (2002) Science 295:868-72. The terms "host cell" and "recombinant host cell" are used interchangeably herein. Such terms refer not only to a particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein so long as they harbor the nucleic acid molecules described herein.

Vector DNA can be introduced into host cells via methods known in the art, e.g., transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell as described herein can be used to produce (i.e., express) a fusion protein as described herein. Methods for producing a KGF-ELP protein using host cells are also described herein. In some embodiments, the methods can include culturing a host cell (into which a recombinant expression vector encoding a fusion protein as described herein has been introduced) in a suitable medium such that a fusion protein, e.g., a KGF-ELP protein, is produced. The methods can further include isolating a fusion protein, e.g., a KGF-ELP protein, from the medium or the host cell.

Purification of the fusion polypeptide can be accomplished using any method known in the art, e.g., using inverse temperature cycling. At lower temperatures, ELPs are soluble in aqueous solutions, however, as the temperature is raised, ELPs undergo an entropically-driven, temperature-induced contraction and self assembly, rendering them insoluble at a critical temperature. This temperature is called the inverse transition temperature, $T_t$. Due to this unique property, ELPs can be expressed in *E. coli* and purified rapidly (Meyer and Chilkoti (1999) Nat Biotechnol 17:1112-1115). KGF-ELP fusions self-assemble into nanoparticles displaying KGF on their periphery at physiological temperatures. These aggregating nanoparticles can be directly injected into the wound site, where they can serve as "drug depots," ensuring a constant supply of recombinant KGF.

Conditions to be Treated

The therapeutic compounds described herein can be used to treat many different open wounds. An open wound is a type of injury in which the skin is torn, cut or punctured. This includes, but is not limited to, burns, recurrent ulcers, incisions, lacerations, abrasions, puncture wounds, penetration wounds, skin graft donor and acceptance sites, and gunshot wounds. The KGF-ELP fusion protein can accelerate recovery of such wounds, including superficial thickness (involving the epidermis), partial thickness (involving the superficial (papillary) or deep (reticular) dermis), and full thickness (involving the epidermis, dermis, and partial damage to subcutaneous fat) wounds.

Burns

Burns may be caused by heat, electricity, chemicals, light, radiation, or friction, and are generally classified accordingly to their seriousness and extent. First degree burns are the mildest and normally only affect the epidermis. The burn site is red, painful, dry, no blisters, very sensitive to touch and the damaged skin may be slightly moist from the leakage of fluid in the deeper layers of the skin. Second degree burns are where both the epidermis and dermis are affected. The damage is deeper and blisters usually appear on the skin. The skin is still painful and sensitive, as the nerves have been affected as well as the sebaceous glands in the area. Third degree burns are the most serious, as the tissues in all layers of the skin are dead. Normally the damaged area goes down into the subcutaneous tissue. In most cases it can penetrate down through the superficial fascia, and into the muscle layers where various arteries and veins may be affected.

Ulcers

KGF has been shown to have a beneficial effect in diabetic ulcers. In particular, foot ulcers are a significant complication of diabetes mellitus and often precede lower-extremity amputation. Approximately 15 to 20 percent of the estimated 16 million persons in the United States with diabetes mellitus will be hospitalized with a foot complication at some time during the course of their disease. The most frequent underlying etiologies are neuropathy, trauma, deformity, high plantar pressures, and peripheral arterial disease.

Other Wounds

Incisions are caused by a clean, sharp-edged object such as a knife, razor or glass splinter. Lacerations are irregular tear-like wounds caused by some blunt trauma. Abrasions are superficial wounds in which the epidermis is scraped off. Puncture wounds are caused by an object puncturing the skin, such as a nail or needle. Penetration wounds may be caused by an object such as a knife entering the body. Gunshot wounds are caused by a bullet or similar projectile driving into or through the body. There may be two wounds, one at the site of entry and one at the site of exit, such is generally known as a through-and-through.

Pharmaceutical Compositions and Methods of Administration

The therapeutic compounds described herein can be incorporated into pharmaceutical compositions. Such compositions typically include the compound (i.e., as an active agent) and a pharmaceutically acceptable carrier. As used herein, "pharmaceutically acceptable carriers" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, or subcutaneous; transdermal (topical), and transmucosal administration. Solutions or suspensions used for parenteral (e.g., intradermal or subcutaneous) application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

For topical compositions, such as cream or gel, suitable carriers and additives include, for example, thickeners, humectants, keratolytics, oils, emollients, surfactants, preservatives, colorants, UV blockers, antioxidants, perfumes, mineral oil, liquid petrolatum, white petrolatum, glycerin, polyethylene glycol, and propylene glycol.

The compositions for administration herein can contain, per dosage unit, e.g., tablet, capsule, powder, injection, teaspoonful and the like, an amount of the active ingredient necessary to deliver an effective amount as described above. A glycerophosphate salt can be formulated in an extended release form suitable for once-weekly or once-monthly administration. Methods are known to those skilled in the art to manufacture the extended release dosage form.

Compositions of the present invention can be formulated at various pH levels would be suitable for purposes of the invention in view of the present disclosure. In preferred embodiments, compositions useful for the present invention have a pH of about 3 to about 10. Compositions for administration herein can be administered in many forms, such as solutions, suspensions, tablets, pills, capsules, spray, gels, drops, sustained release formulations, powders or active ingredient impregnated bandages.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, compositions for administration herein are administered to a subject topically. Creams, gels, ointments, powders, aerosols and solutions are suitable for topical administration. Preferably, the compositions are dermatologically acceptable and do not cause significant skin irritation under normal usage circumstances with typical patients when the compositions are applied to the skin. Compositions containing a glycerophosphate salt suitable for topical administration have been described, for example, in U.S. Pat. No. 5,972,321, which is incorporated herein by reference.

In one embodiment for topical administration, the composition for administration comprises one or more glycerophosphate salts, a solvent, and at least one excipient selected from thickeners, humectants, keratolytics, oils, emollients, surfactants, preservatives, colorants, UV blockers, antioxidants, perfumes, mineral oil, liquid petrolatum, white petrolatum, glycerin, polyethylene glycol and propylene glycol. A thickener can be any agent useful as an aid to thicken or add structure to a topical formulation, or to result in a viscosity suitable for dermatologic applications. Non-limiting examples of thickening agents are gums and natural polysaccharides, mineral thickeners, oils, and synthetic polymeric thickeners.

In one embodiment for topical administration, the composition for administration comprises one or more solvents in an amount of about 10% to about 90% by weight, one or more glycerophosphate salts in a total amount of about 0.001% to about 25% by weight, a polymeric thickener in an amount of about 0.05% to about 5% by weight. The solvent is preferably nonalcoholic. The polymeric thickener can be a polyacrylic acid thickener or an alkylhydroxycellulose thickener.

In one embodiment for topical administration, the composition for administration further contains a preservative. Preferably the preservative is food grade or pharmaceutical grade. Examples of preservatives that can be used in the composition include, but are not limited to, methylparaben, ethylparaben, butylparaben, propylparaben, and any other preservative that is typically used in water-based cosmetics, such as creams and lotions and some bath products. The preservative is present at an amount that is sufficient to prevent the composition from supporting the growth of microbes such as bacteria, fungi, or yeasts.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

Dosage, toxicity, and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The pharmaceutical compositions can be included in a container, pack, or dispenser together with instructions for administration.

EXAMPLES

The invention is further described in the following examples, which do not limit the scope of the invention described in the claims.

Example 1

Synthesis of KGF-ELP Fusion Protein

Human recombinant KGF was cloned at the N terminus of the elastin like peptide (ELP, $V_{40}C_2$) encoding cassette (FIG. 1A) within the pUC19 vector. The plasmid pUC19 containing the elastin cassette $V_{40}C_2$ has been described previously (Huang et al. (2008) Langmuir 24:14139-44). The plasmid containing the KGF cDNA has also been previously described (Andreadis et al. (2001) FASEB J 15:898-906). The KGF coding sequence was PCR amplified using primers having PflMI and BglI sites at the 5' and 3' ends, respectively, using PfuUltra high fidelity polymerase (Stratagene, La Jolla, Calif.) as per manufacturer's recommendations. Briefly, 10 ng of the plasmid was used per reaction and the PCR amplified fragment was then cloned using a zero blunt TOPO PCR cloning kit (Invitrogen, Carlsbad, Calif.) as per manufacturer's recommendations. After TOPO cloning, the KGF fragment was excised using PflMI and BglI enzymes. The pUC19 vector containing the $V_{40}C_2$ sequence was linearized by PflMI and the excised KGF fragment was then cloned in frame with the elastin cassette. This yielded a pUC19 vector containing the KGF-ELP fusion sequence. This sequence encoding the fusion protein was then cut out using PflMI and BglI enzymes and cloned in a modified pET25b+ expression vector via a SfiI site. An elastin cassette containing 50 elastin pentapeptides was used because this cassette has a transition temperature lower than physiological temperature (Meyer and Chilkoti (2002) Biomacromolecules 3:357-367).

The pET25b+ vector containing the KGF-ELP sequence cassette was transformed into *E. coli* BLR (Stratagene, La Jolla, Calif.) cells and purified using inverse temperature cycling. A starter culture of 50 mL was then inoculated overnight in terrific broth. The next day, the 50 mL culture was added to a 1 L culture. The 1 L culture was then propagated overnight in an incubator shaker at 250 rpm and 37° C. Bacterial cells were harvested by centrifugation at 4° C. the next day. The bacterial pellet was resuspended in 1× phosphate buffered saline (PBS), and the cells were disrupted by sonication on ice. The lysate was cleared by centrifugation followed by a polyethyleneimine treatment (0.5% w/v final concentration) in order to precipitate soluble nucleic acids. After another round of centrifugation to pellet nucleic acids, the cleared supernatant containing KGF-ELP was transferred to a clean centrifuge tube. The tube was heated to 40° C. in the presence of 1M NaCl to precipitate the ELP. A warm centrifugation at 40° C. was carried out to pellet KGF-ELP. The supernatant was then discarded, and the pellet was resolubilized in PBS in the presence of 10 mM DTT on ice. Another cold spin at 4° C. was performed to get rid of insoluble contaminants. This cycle was repeated two more times yielding a total of three cycles of inverse temperature cycling. For the final resuspension step, the KGF-ELP was re-suspended in purified water. This KGF-ELP was then dialyzed overnight against deionized water at 4° C. using a Spectra/Por 14 kDa cutoff membrane (Spectrum Laboratories, Laguna Hills, Calif.) to remove contaminating salts. Samples were saved after the completion of each cycle. After salt removal, the protein was lyophilized using a Virtis Advantage lyophilizer (Virtis, Gardiner, N.Y.) and stored at room temperature for further analysis.

Three cycles of inverse temperature cycling yielded a highly purified protein with minimum contamination. The bacterial lysate, supernatant, and the lyophilized protein were resuspended in lysis buffer (Cell Signaling Technologies, Danvers, Mass.) supplemented with DTT and a cocktail of protease inhibitors (Roche Diagnostics GmbH, Mannheim, Germany). Purified lyophilized protein was dissolved in purified water and further diluted with sample buffer (Cell Signaling technology) for gel loading. The protein samples were separated by SDS-PAGE (8%) and transferred to nitrocellulose membrane (transfer buffer: 25 mM Tris-HCl, pH 8.3, 192 mM glycine, 20% (v/v) methanol) for 1 hour at 350 mA using an electrophoretic transfer cell (Mini Trans-Blot®; BioRad Laboratories, Hercules, Calif.). The membranes were blocked with blocking buffer containing 5% (w/v) non-fat dry milk in TBS-Tween (20 mM Tris-HCl, pH 7.2-7.4, 150 mM NaCl, 0.1% (v/v) Tween 20) on a rocker platform for 1 hour at room temperature. Membranes were incubated with mouse anti-human recombinant KGF (1 µg/mL in 5% BSA, R&D Systems) overnight at 4° C. After washing 3 times for 5 minutes, the membranes were incubated with HRP-conjugated anti-mouse (1:2,000 dilution in 5% nonfat dry milk, 1 hour at room temperature, Cell Signaling Technology). After washing 3 times, protein bands were detected using chemiluminescence (LumiGLO; Cell Signaling Technology) as per manufacturer's instructions and exposed to film. Western blot analysis of the KFG-ELP fusion peptide yielded a protein band at about 43 kDa, similar to the expected molecular weight of the protein (FIG. 1B).

Example 2

Formation of KGF-ELP Particles

ELPs undergo an entropically driven contraction and self assembly, rendering them insoluble above a transition temperature ($T_t$). This property of ELPs was maintained in the fusion protein and the protein was purified from bacterial lysates using ITC (FIG. 1B). The fusion protein consists of two regions: the hydrophilic KGF domain and the hydrophobic elastin domain, essentially forming a hydrophilic-hydrophobic block co-polymer. Therefore, as described previously for other ELP block copolymers (Dreher et al. (2008) J Am Chem Soc 130:687-694), spherical micellar particles displaying KGF at their periphery should be formed at $T_t$, when the ELP block self-associates to form a hydrophobic core. To assess the formation of particles, KGF-ELP was suspended in saline and particle formation was allowed to occur at 37° C. for 2 minutes. These particles were imaged by TEM, which showed spherical particles with a diameter of 500 nm (FIG. 2A). The diameter of these particles was about 500 nm as measured by dynamic light scattering using ZetaPALS, Zeta Potential Analyzer (Brookhaven Instruments Corporation, Holtsville, N.Y.). Moreover, the particles were fairly monodispersed (FIG. 2B).

To assess the effect of temperature on the precipitated particles, the diameter of the formed particles was measured over a range of temperatures using dynamic light scattering. KGF-ELP exists as a monomer at lower temperatures as suggested by a small diameter, and as the temperature is raised, the ELP chains come together and form particles with a diameter of 500-600 nm. These remained as particles over a wide range of temperatures (from 30 to 60° C.) with very low poly dispersity (FIG. 2C). This suggests that KGF-ELP particles can be used for delivery at temperatures as low as 30° C. This low transition temperature is critical for their application as growth factor delivery vehicles as skin temperature is often below 37° C.

The lyophilized KGF-ELP was re-suspended in PBS at a concentration of 1.0 mg/mL. The ELP solution was then incubated at 37° C. for 2-3 minutes to form particles. The particles were adsorbed on glow discharged carbon coated grids and were stained with 1% uranyl formate staining solution. The stained particles were then imaged at the Conventional Microscopy Core at the Department of Cell Biology at Harvard Medical School using a Tecnai™ $G^2$ Spirit BioTWIN microscope (FEI Hilsboro, Oreg.).

Example 3

KGF-ELP Induces Proliferation in Cells

Originally identified as a potent mitogen of keratinocytes (Rubin et al. (1989) Proc Natl Acad Sci USA 86:802-806), KGF is a powerful enhancer of epithelial regeneration (Werner (1998) Cytokine & Growth Factor Rev 92:153-165). To assess the biological activity of recombinant KGF in the KGF-ELP fusion, a proliferation assay was carried out using a KGF responsive epithelial cell line A431 (Koria and Andreadis (2007) Am J Physiol 293:C1020-1031). A431 cells were plated (50,000 cells/well) in 48-well plates and serum starved overnight before addition of the KGF-ELP particles. The particles were formed by dissolving KGF-ELP or control ELP in serum free media on ice (DMEM supplemented with 1% BSA). The ELP solution was then incubated at 37° C. for 2 minutes to initiate particle formation, and placed on top of the serum starved cells. Two days after addition of KGF-ELP particles, the cells were washed twice with ice-cold PBS, and 200 µl water was added followed by three freeze and thaw cycles to lyse the cells. Cell lysate (100 µl) was mixed with 100 µl of Hoechst 33258 (1:400 dilution in THE buffer; Molecular Probes, Eugene, Oreg.) and fluorescence intensity was measured in a fluorescence microplate reader (SpectraMax Gemini, Molecular Devices, Menlo Park, Calif.).

KGF-ELP induced proliferation in the cells after two days (FIG. 3A, 2.31-fold, $p<0.05$), while ELP by itself had no effect on keratinocyte proliferation. Furthermore, KGF-ELP phosphorylated the downstream targets of KGF, ERK1 and ERK2 (Koria and Andreadis (2007) Am J Physiol 293: C1020-1031) (FIG. 3B). These data demonstrate that the activity of KGF in the fusion protein was retained.

Figure 3C:
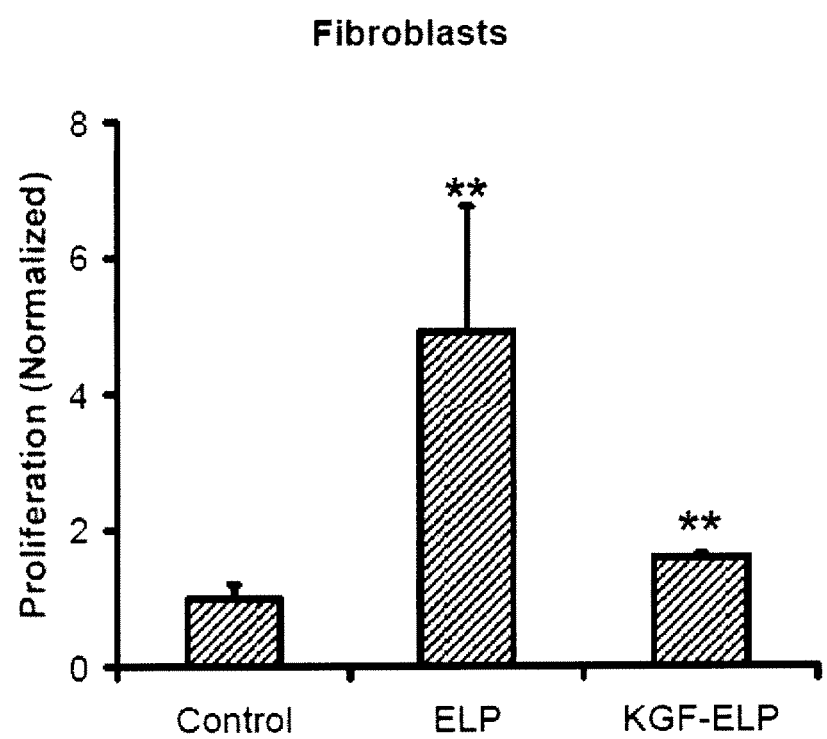

Similarly, previous studies have indicated that elastin induces proliferation of fibroblasts (Kamoun et al. (1995) Cell Adhesion and Communication 3:273-281). To test the biological activity of ELPs, ELPs or KGF-ELP were added to serum-starved fibroblasts. Indeed after two days, ELPs induced a dramatic 4.9-fold increase in fibroblast proliferation (FIG. 3C, $p<0.05$). On the other hand, the fusion protein KGF-ELP showed a 1.6-fold increase in fibroblast proliferation (FIG. 3C, $p<0.05$), confirming that biological activity of ELP was maintained in the fusion.

Example 4

KGF-ELP Enhances Wound Healing in Primary Keratinocytes

Figure 4:
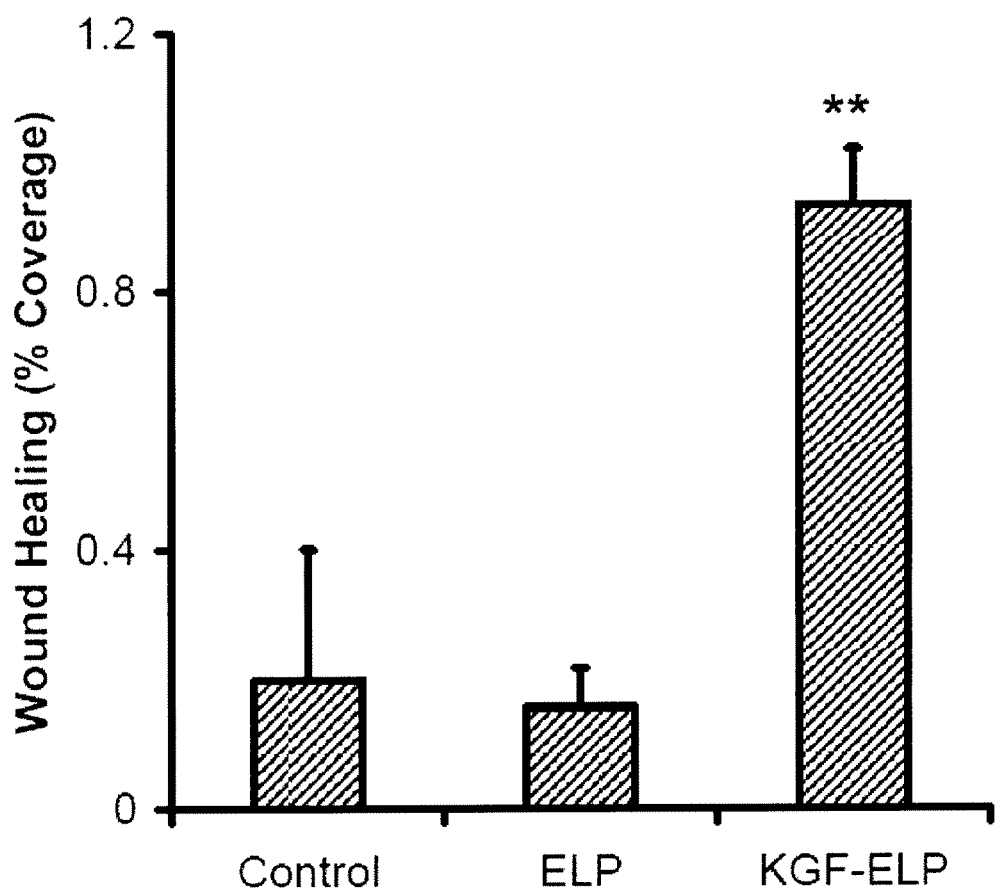
FIG. 4 is a bar graph showing that KGF-ELP particles improve wound healing in primary keratinocytes. Scratch wound assays were set up by wounding confluent primary keratinocyte monolayers with a pipette tip. After wounding, the cells were washed with saline and were treated with the indicated treatments. The covered wound areas were measured and normalized by the area measured at time t=0. This experiment was repeated twice with quadruplicate samples and a representative experiment is shown (**indicates p<0.05).

The efficacy of KGF-ELP particles was evaluated in an in vitro scratch wound model comprised of primary keratinocytes as described previously (Koria and Andreadis (2007) Am J Physiol 293:C1020-1031). Primary keratinocytes (150, 000 cells/well) were seeded in 24-well plates in K-SFM (Invitrogen, Carlsbad, Calif.). After they reached confluence, the monolayer was scratched using a 1 mL pipette tip. The cells were washed twice with PBS to remove cellular debris, and K-SFM supplemented with high $Ca^{2+}$ (2 mM), Control-ELP (ELP, 10 µg/mL or 23 nM), or KGF-ELP particles formed in K-SFM (KGF-ELP, 10 µg/mL or 23 nM) was added to the wounded monolayers. Healing was quantified by measuring the open wound area remaining after 4 days. At 96 hours post-wounding, while there was little healing in the control ELP samples (FIG. 4), cells treated with KGF-ELP particles showed almost complete healing (FIG. 4). Keratinocytes without treatment (control) and those treated with ELP showed only 15-20% coverage, while cells treated with KGF-ELP showed close to 93% coverage ($p<0.05$, FIG. 4). Images of the wounds were acquired at 4× magnification on an inverted microscope (Olympus CKX41, Olympus, Center Ville, Pa.) using a Retiga 2000R digital camera (QImaging, Burnaby, BC, Canada). The area of the wound was quantified using ImageJ 1.28 k software (National Institutes of Health, USA) and percent healing was defined as the area of the wound occupied by cells over the initial wound area.

Example 5

KGF-ELP Particles Improve Healing of a Full Thickness Wound

Genetically diabetic male B6.BKS(D)-Lepr$^{db}$/J mice were obtained from The Jackson Laboratory (Bar Harbor, Me.). This naturally occurring mutation causes insulin resistance and significantly retards wounds healing. All mice were 9 weeks old at the time of wounding. Each mouse was housed individually. The animals were cared for in accordance with the guidelines set forth by the Committee on Laboratory Resources, National Institutes of Health, and Subcommittee on Research Animal Care and Laboratory Animal Resources of Massachusetts General Hospital. All animals had free access to food and water, both before and after the operation.

The efficacy of KGF-ELP in treatment of full thickness diabetic wound models was assessed by first creating a full thickness wound. The diabetic mice were anesthetized using 2 to 2.5% vaporized inhaled isoflurane (Iso Flo, Abbott Laboratories, North Chicago, Ill.). Under sterile conditions, the dorsal area was totally depilated and a single full-thickness excisional square wound (1×1 cm²) was created on the upper back of each mouse using a pair of sharp scissors and a scalpel. 100 μl of Fibrin gel containing either 1 mg/mL KGF-ELP or Control-ELP, prepared as described below, was administered into the wounds of the mice and dressed with a 2.5 cm×2.5 cm piece of Tegaderm™ (3M Health Care, St Paul, Minn.). After 14 days of the administration of the gels, the mice were euthanized using pentobarbital anesthesia. The skin around the wound was then excised and processed further for histology. The excised tissue was embedded in paraffin and 6 μm tissue sections were cut and mounted on slides. The sections were stained for hematoxylin and eosin. Pictures of the wound were then taken using a Nikon Microscope. The length and thickness of the tissue were measured using ImageJ 1.28 k software.

Fibrin gels were prepared by mixing two fractions: one containing fibrinogen (6.25 mg/mL, Sigma), KGF-ELP (0.45 nM), KGF (0.023 nM), or ELP (0.45 nM), and the other containing thrombin (12.5 U/mL, Sigma) and $CaCl_2$ (12.5 mmol/L) in 1× Tris buffered saline. The ELP dissolved in fibrinogen was incubated at 37° C. for formation of particles prior to the formation of fibrin gels. After wounding the mice, 80 μL of the warm fibrinogen fraction containing the particles was mixed with 20 μL of the thrombin fraction in a tube and immediately applied to the wound topically. After the mixture was gelled (in <2 minutes), wounds were covered with Tegaderm™ (3M Health Care, St Paul, Minn.).

FIG. 5 shows the appearance of the wound after 14 days. While wounds treated with fibrin gel alone (FIG. 5A) or those treated with KGF in fibrin gel (FIG. 5B) failed to heal (see the wound edge denoted by arrowheads), mice treated with ELP or KGF-ELP nanoparticles showed significant tissue formation in the middle of the wound (FIGS. 5C and 5D). Interestingly, wounds treated with ELP still exhibited wound edges (FIG. 5C, arrowheads) and showed significant granulation in the middle (FIG. 5C). Furthermore, the wound edges were almost invisible in the mice treated with the KGF-ELP nanoparticles (FIG. 5D).

Figure 7E:
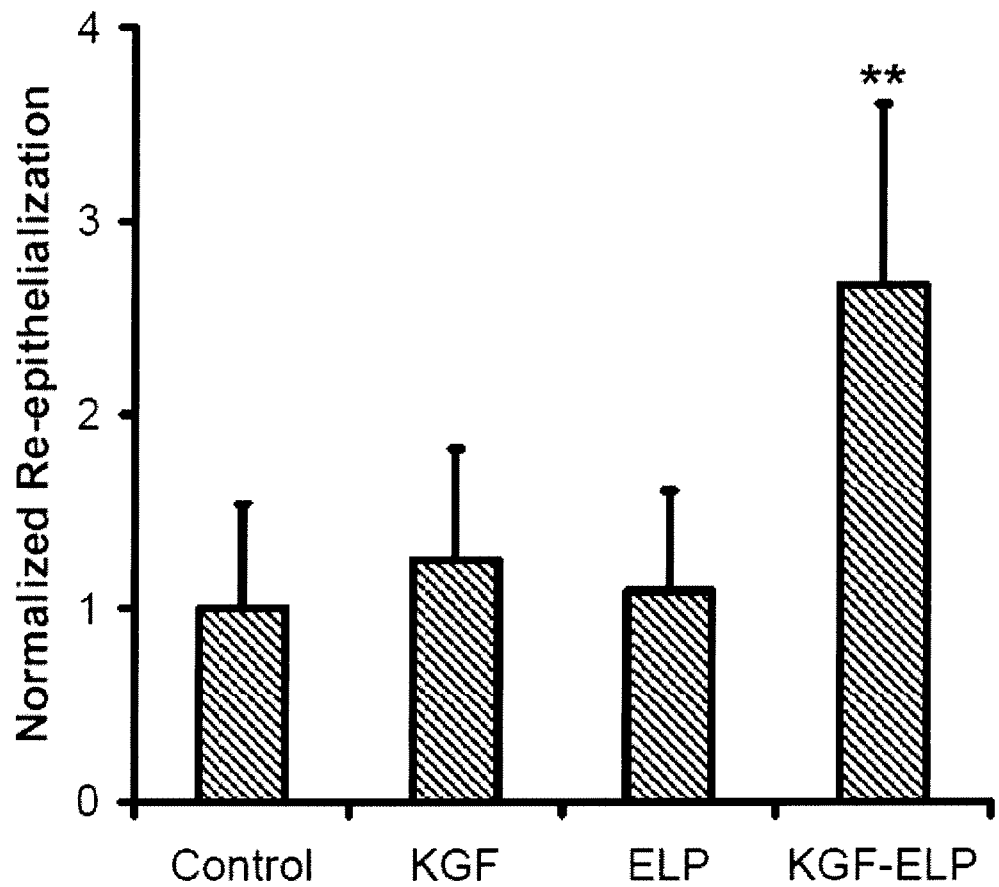

Further histological examination revealed that the wounds treated with ELP and KGF-ELP particles exhibited thicker granulation tissue as compared to the other treatments (FIG. 6). The granulation tissue was much thicker in the wounds treated with ELP or KGF-ELP, 5-fold or 3-fold increase compared to control, respectively (FIG. 6E, $p<0.05$, n=7). Since fibroblasts are one of the main components of granulation tissue, these results demonstrate that ELPs enhance granulation by inducing fibroblast proliferation. This is further supported by the induction of less granulation by KGF-ELP since the in vitro data showed less fibroblast proliferation induced by KGF-ELPs than ELP alone (FIG. 3C). On the other hand, only wounds treated with KGF-ELP nanoparticles showed significant re-epithelialization (FIGS. 7A-D). KGF-ELP treatment increased the extent of re-epithelialization by 2-fold over all other treatments (FIG. 7E, $p<0.05$, n=7).

REFERENCES

Barrientos S, Stojadinovic O, Golinko M S, Brem H, Tomic-Canic M. Wound Repair Regen 2008 September-October; 16(5):585-601.
Byrnes C K, Khan F H, Nass P H, Hatoum C, Duncan M D, Harmon J W. Wound Repair Regen 2001 September-October; 9(5):341-346.
Herrero-Vanrell R, Rincon A C, Alonso M, Reboto V, Molina-Martinez I T, Rodriguez-Cabello J C. J Control Release 2005 Jan. 20; 102(1):113-122.
Leahy P J, Lawrence W T. Clinics in Plastic Surgery 2007 October; 34(4):659-671.
Osborne J L, Farmer R, Woodhouse K A. Acta Biomaterialia 2008 January; 4(1):49-57.
Papanas N, Maltezos E. The International Journal of Lower Extremity Wounds 2007 March; 6(1):37-53.
Petrie N C, Vranckx J J, Hoeller D, Yao F, Eriksson E. Journal of Tissue Viability 2005 November; 15(4):16-21.
Rincon A C, Molina-Martinez I T, de Las Heras B, Alonso M, Bailez C, Rodriguez-Cabello J C, et al. Journal of Biomedical Materials Research 2006 August; 78(2):343-351.
Saba A A, Freedman B M, Gaffield J W, Mackay D R, Ehrlich H P. Annals of Plastic Surgery 2002 July; 49(1):62-66; discussion 66.
Shamji M F, Betre H, Kraus V B, Chen J, Chilkoti A, Pichika R, et al. Arthritis and Rheumatism 2007 November; 56(11):3650-3661.
Shamji M F, Chen J, Friedman A H, Richardson W J, Chilkoti A, Setton L A. J Control Release 2008 Aug. 7; 129(3):179-186.
Steed D L. Plastic and Reconstructive Surgery 2006 June; 117(7 Suppl):143S-149S; discussion 150S-151S.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified polypeptide comprising a keratinocyte growth factor (KGF) linked to an elastin-like peptide (ELP), wherein the polypeptide comprises an amino acid sequence that is at least 98% identical to SEQ ID NO:2.

2. The purified polypeptide of claim 1, wherein the polypeptide is in a topical formulation.

3. The purified polypeptide of claim 2, wherein the topical formulation is a cream or gel.

4. A method of producing a keratinocyte growth factor-elastin-like peptide (KGF-ELP) particle, the method comprising providing a polypeptide comprising a KGF linked to an ELP wherein the polypeptide comprises an amino acid sequence that is at least 98% identical to SEQ ID NO:2, and incubating the polypeptide at a temperature of 30° C. to 60° C.

5. A KGF-ELP particle produced by the method of claim 4.

6. The polypeptide of claim 1, wherein the polypeptide comprises amino acids 201-206 of SEQ ID NO:2 consisting of the sequence YSPGVG (SEQ ID NO:3).

7. The polypeptide of claim 1, wherein the polypeptide comprises the amino acid sequence of SEQ ID NO:2.

8. The polypeptide of claim 1, wherein the KGF comprises an amino acid sequence that is at least 98% identical to amino acids 7-200 of SEQ ID NO:2.

9. The polypeptide of claim 1, wherein the ELP comprises an amino acid sequence that is at least 98% identical to amino acids 207-456 of SEQ ID NO:2.

10. The polypeptide of claim 1, wherein the polypeptide comprises an amino acid sequence that is at least 99% identical to SEQ ID NO:2.

11. The polypeptide of claim 1, wherein the KGF comprises an amino acid sequence that is at least 99% identical to amino acids 7-200 of SEQ ID NO:2.

12. The polypeptide of claim 1, wherein the ELP comprises an amino acid sequence that is at least 99% identical to amino acids 207-456 of SEQ ID NO:2.

\* \* \* \* \*